United States Patent [19]

Hanson

[11] Patent Number: 5,461,074
[45] Date of Patent: Oct. 24, 1995

[54] USE OF DI-PROPARGYL-CONTAINING ARYL/ALKYLSULFONYL-TERMINATED ALANINE AMINO-DIOL COMPOUNDS FOR TREATMENT OF HYPERTENSION

[75] Inventor: Gunnar J. Hanson, Skokie, Ill.

[73] Assignee: G.D. Searle & Co., Chicago, Ill.

[21] Appl. No.: 110,447

[22] Filed: Aug. 23, 1993

Related U.S. Application Data

[62] Division of Ser. No. 916,571, Jul. 20, 1992, Pat. No. 5,246,969.

[51] Int. Cl.$^6$ ............ A61K 31/16; A61K 31/165
[52] U.S. Cl. ............................................. 514/616
[58] Field of Search ..................... 514/616; 564/154

[56] References Cited

U.S. PATENT DOCUMENTS

| | | | |
|---|---|---|---|
| 4,902,706 | 2/1990 | Hanson et al. | 514/400 |
| 4,914,129 | 4/1990 | Bühlmayer et al. | 514/616 |
| 5,032,577 | 7/1991 | Fung et al. | 514/18 |
| 5,246,969 | 9/1993 | Hanson et al. | 514/616 |

FOREIGN PATENT DOCUMENTS

| | | |
|---|---|---|
| 30797/89 | 9/1989 | Australia . |
| 128762 | 12/1984 | European Pat. Off. . |
| 181110 | 5/1986 | European Pat. Off. . |
| 189203 | 7/1986 | European Pat. Off. . |
| 186977 | 7/1986 | European Pat. Off. . |
| 200406 | 12/1986 | European Pat. Off. . |
| 216539 | 4/1987 | European Pat. Off. . |
| 229667 | 7/1987 | European Pat. Off. . |
| 300189 | 1/1989 | European Pat. Off. . |
| 416373 | 3/1991 | European Pat. Off. . |
| 87/04349 | 7/1987 | WIPO . |

OTHER PUBLICATIONS

Umezawa et al, in *J. Antibiot.* (Tokyo), 23, 259–262 (1970).
Gross et al, *Science*, 175, 656 (1971).
Boger et al, *Nature*, 303, 81 (1983).
Kokubu et al, *Biochm. Biophys. Res. Commun.*, 118, 929 (1984).
Castro et al, *FEBS Lett.*, 167, 273 (1984).
Hanson et al, *Biochm. Biophys. Res. Comm.*, 132, 155–161 (1985), 146, 959–963 (1987).

*Primary Examiner*—Richard L. Raymond
*Attorney, Agent, or Firm*—J. Timothy Keane

[57] ABSTRACT

Diseases mediated by plasma renin activity may be treated with a compound characterized generally as a di-propargyl-containing aryl/alkylsulfonyl-terminated amino diol derivative. Compounds of particular interest are those of the formula

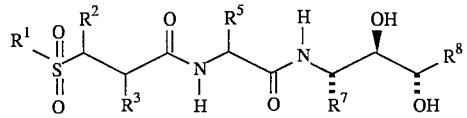

wherein $R^1$ is selected from isopropyl, isobutyl, sec-butyl, tert-butyl, phenyl, fluorophenyl, chlorophenyl, benzyl, fluorobenzyl, chlorobenzyl, naphthyl, fluoronaphthyl, chloronaphthyl, fluoronaphthylmethyl and chloronaphthylmethyl; wherein $R^2$ is selected from hydrido, methyl, ethyl and phenyl; wherein $R^3$ is selected from hydrido, cyclohexylmethyl, benzyl, fluorobenzyl, chlorobenzyl, fluoronaphthylmethyl and chloronaphthylmethyl; wherein each of $R^5$ and $R^8$ is independently propargyl or a propargyl-containing moeity; and wherein $R^7$ is cyclohexylmethyl.

10 Claims, No Drawings

USE OF DI-PROPARGYL-CONTAINING ARYL/ALKYLSULFONYL-TERMINATED ALANINE AMINO-DIOL COMPOUNDS FOR TREATMENT OF HYPERTENSION

This is a divisional of application Ser. No. 07/916,571 filed Jul. 20, 1992, now U.S. Pat. 5,243,909, now U.S. Pat. No. 5,246,969.

FIELD OF THE INVENTION

Renin-inhibiting compounds are known for control of hypertension. Of particular interest herein are compounds useful as renin inhibiting agents.

BACKGROUND OF THE INVENTION

Renin is a proteolytic enzyme produced and secreted into the bloodstream by the juxtaglomerular cells of the kidney. In the bloodstream, renin cleaves a peptide bond in the serum protein angiotensinogen to produce a decapeptide known as angiotensin I. A second enzyme known as angiotensin converting enzyme, cleaves angiotensin I to produce the octapeptide known as angiotensin II. Angiotensin II is a potent pressor agent responsible for vasoconstriction and elevation of cardiovascular pressure. Attempts have been made to control hypertension by blocking the action of renin or by blocking the formation of angiotensin II in the body with inhibitors of angiotensin I converting enzyme.

Classes of compounds published as inhibitors of the action of renin on angiotensinogen include renin antibodies, pepstatin and its analogs, phospholipids, angiotensinogen analogs, pro-renin related analogs and peptide aldehydes.

A peptide isolated from actinomyces has been reported as an inhibitor of aspartyl proteases such as pepsin, cathepsin D and renin [Umezawa et al, in *J. Antibiot.* (Tokyo), 23, 259–262 (1970)]. This peptide, known as pepstatin, was found to reduce blood pressure in vivo after the injection of hog renin into nephrectomized rats [Gross et al, *Science,* 175, 656 (1971)]. Pepstatin has the disadvantages of low solubility and of inhibiting acid proteases in addition to renin. Modified pepstatins have been synthesized in an attempt to increase the specificity for human renin over other physiologically important enzymes. While some degree of specificity has been achieved, this approach has led to rather high molecular weight hepta- and octapeptides [Boger et al, *Nature,* 303, 81 (1983)]. High molecular weight peptides are generally considered undesirable as drugs because gastrointestinal absorption is impaired and plasma stability is compromised.

Short peptide aldehydes have been reported as renin inhibitors [Kokubu et al, *Biochim. Biophys, Res. Common.,* 118, 929 (1984); Castro et al, *FEBS Lett.,* 167, 273 (1984)]. Such compounds have a reactive C-terminal aldehyde group and would likely be unstable in vivo.

Other peptidyl compounds have been described as renin inhibitors. EP Appl. #128,762, published 18 Dec. 1984, describes dipeptide and tripepride glyco-containing compounds as renin inhibitors [also see Hanson et al, *Biochm, Biophys, Res. Comm.,* 132, 155–161 (1985), 146, 959–963 (1987)]. EP Appl. #181,110, published 14 May 1986, describes dipeptide histidine derivatives as renin inhibitors. EP Appl. #186,977 published 9 Jul. 1986 describes renin-inhibiting compounds containing an alkynyl moiety, specifically a propargyl glycine moiety, attached to the main chain between the N-terminus and the C-terminus, such as N-[4(S)-[(N)-[bis(1-naphthylmethyl)acetyl]-DL-propargylglycylamino]- 3(S)-hydroxy-6-methylheptanoyl]-L-isoleucinol. EP Appl. #189,203, published 30 Jul. 1986, describes peptidyl-aminodiols as renin inhibitors. EP Appl. #200,406, published 10 Dec. 1986, describes alkylnaphthylmethylpropionyl-histidyl aminohydroxy alkanoates as renin inhibitors. EP Appl. #216,539, published 1 Apr. 1987, describes alkylnaphthylmethylpropionyl aminoacyl aminoalkanoate compounds as renin inhibitors orally administered for treatment of renin-associated hypertension. PCT Application No. WO 87/04349, published 30 Jul. 1987, describes aminocarbonyl aminoacyl hydroxyether derivatives having an alkylamino-containing terminal substituent and which are described as having renin-inhibiting activity for use in treating hypertension. EP Appl. #300,189 published 25 Jan. 1989 describes amino acidmonohydric derivatives having an alkylamino-alkylamino N-terminus and a β-alaninehistidine or sarcosyl-histidine attached to the main chain between the N-terminus and the C-terminus, which derivatives are mentioned as useful in treating hypertension. U.S. Pat. No. 4,902,706 which issued 13 Feb. 1990 describes a series of histidineamide-containing amino alkylaminocarbonyl-H-terminal aminodiol derivatives for use as renin inhibitors. U.S. Pat. No. 5,032,577 which issued 16 Jul. 1991 describes a series of histidineamide-aminodiol-containing renin inhibitors.

Several classes of sulfonyl-containing amino-diol renin-inhibitor compounds are known. For example, EP #229,667 published 22 Jul. 1987 describes generally alkylsulfonyl histidineamide amino diol C-terminated-alkyl compounds as renin inhibitors. Australian Patent Application #30797/89 published 7 Sep. 1989 describes alkylsulfonyl histineamide amino diol C-terminated-alkyl compounds as renin inhibitors, such as (S)-α-[(S)-α-[(t-butylsulphonyl)methyl] hydrocinnamamido]-N-[(1S,2R,3RS)-1-(cyclohexylmethyl)- 2,3-dihydroxy-4,4-dimethylpentyl]-imidazole- 4-propionamide and (S)-α-[(S)-α-[(t-butylsulphonyl)methyl] hydrocinnamamido]-N-[(1S,2R, 3S, 4RS)-1-(cyclohexylmethyl)- 2,3-dihydroxy-4-methylhexyl]imidazole-4-propionamide. U.S. Pat. No. 4,914,129 issued 3 Apr. 1990 describes sulfone-containing amino-hydroxyvaleryl compounds for use as antihypertensive agents, such as the compounds N[ 2(S)-benzyl-3-tert-methylsulfonylpropionyl]-His-Cha-Val-n-butylamide and N-[2(R)-benzyl-3-tert-methylsulfonylpropionyl]-His-Cha-Val-n-butylamide. EP #416,373 published 13 Mar. 91 describes alkylsulfonyl histidineamide amino diol compounds as renin-inhibitors, such as (S)-α-[(S)-α-[(tert-butylsulfonyl)methyl]hydrocinnamamido]-N-[ (1S,2R,3S)-1-(cyclohexylmethyl)-3-cyclopropyl- 2,3-dihydroxypropyl] -imidazol-4-propionamide and (S)-α-[(S)-α-[(tert-butylsulfonyl)methyl]-hydrocinnamamido] -N-[ (1S,2R,3R/S)-1-(cyclohexylmethyl)-3-cyclopropyl-2,3-dihydroxybutyl]imidazol- 4-propionamide.

Propargyl-containing amino diol compounds for treatment of hypertension are described in U.S. Application Ser. No. 07/783,955 of G. J. Hanson et al filed on 29 Oct. 1991.

DESCRIPTION OF THE INVENTION

Di-propargyl-containing aryl/alkylsulfonyl-terminated alanine amino diol compounds, having utility as renin inhibitors for treatment of hypertension in a subject, constitute a family of compounds of general Formula I:

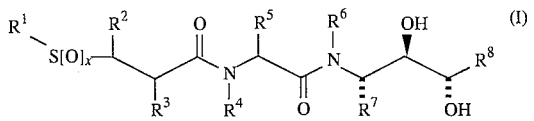

The term "di-propargyl-containing" characterizes these compounds as having a propargyl group or a propargyl-containing group attached at the P2 substitution site of the backbone of Formula I, i.e., at the $R^5$ position, as well as having a propargyl group or a propargyl-containing group at the C-terminus of the Formula I structure, i.e., at the $R^8$ position. These Formula I compounds may be further characterized as forming a family of renin inhibitors wherein $R^1$ is a group selected from alkyl, trifluoromethyl, cycloalkyl, cycloalkylalkyl, aryl, haloaryl, aralkyl and haloaralkyl; wherein x is a number selected from zero, one and two; wherein $R^2$ is selected from hydrido and alkyl; wherein $R^3$ is a group selected from hydrido, cycloalkylalkyl, aralkyl and haloaralkyl; wherein each of $R^4$ and $R^6$ is a group independently selected from hydrido and methyl; wherein each of $R^5$ and $R^8$ is independently a propargyl moiety or a propargyl-containing moiety selected from

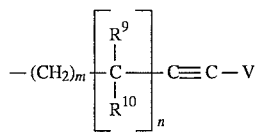

wherein V is selected from hydrido, alkyl, cycloalkyl, aryl and aralkyl; wherein each of $R^9$ and $R^{10}$ is a group independently selected from hydrido, alkyl, alkenyl, alkynyl, cycloalkyl and aryl; wherein m is a number selected from zero through three; wherein n is a number selected from zero through three; wherein $R^7$ is a group selected from alkyl, cycloalkylalkyl and aralkyl; and wherein any one of said $R^1$ through $R^{10}$ groups having a substitutable position may be substituted with one or more groups selected from alkyl, hydroxy, alkoxy and alkenyl.

A preferred family of compounds consists of compounds of Formula I wherein $R^1$ is selected from alkyl, trifluoromethyl, cycloalkyl, cycloalkylalkyl, phenyl, halophenyl, phenylalkyl, halophenylalkyl, naphthyl, halonaphthyl, naphthylaklyl and halonaphthylalkyl; wherein x is a number selected from zero, one and two; wherein $R^2$ is selected from hydrido and alkyl; wherein $R^3$ is selected from hydrido, cycloalkylalkyl, phenylalkyl, halophenylalkyl, naphthylalkyl and halonaphthylalkyl; wherein each of $R^4$ and $R^6$ is independently selected from hydrido and methyl; wherein each of $R^5$ and $R^8$ is independently propargyl moiety or a propargyl-containing moiety selected from

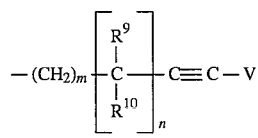

wherein V is selected from hydrido, alkyl, phenyl and benzyl; wherein each of $R^9$ and $R^{10}$ is independently selected from hydrido, alkyl, alkenyl, alkynyl, cycloalkyl and aryl; wherein m is a number selected from zero through three; wherein n is a number selected from zero through three; and wherein $R^7$ ms selected from cyclohexylmethyl and benzyl, either one of which may be substituted with one or more groups selected from alkyl, hydroxy and alkoxy.

A more preferred family of compounds consists of compounds of Formula I wherein $R^1$ is selected from methyl, ethyl, n-propyl, isopropyl, n-butyl, isobutyl, sec-butyl, tert-butyl, trifluoromethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is a number selected from zero, one and two; wherein $R^2$ is selected from hydrido, methyl, ethyl and n-propyl; wherein $R^3$ is selected from hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is independently selected from hydrido and methyl; wherein each of $R^5$ and $R^8$ is independently selected from

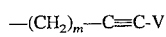

wherein V is selected from hydrido and alkyl; wherein m is a number selected from one through three; and wherein $R^7$ is cyclohexylmethyl.

An even more preferred family of compounds consists of compounds Formula I wherein $R^1$ is selected from methyl, ethyl, n-propyl, isopropyl, benzyl, phenethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is zero or two; wherein $R^2$ is selected from hydrido, methyl, ethyl and n-propyl; wherein $R^3$ is selected from hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is hydrido; wherein each of $R^5$ and $R^8$ is independently selected from

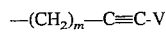

wherein V is selected from hydrido and methyl; wherein m is one or two; and wherein $R^7$ is cyclohexylmethyl.

A highly preferred family of compounds consists of compounds of Formula II

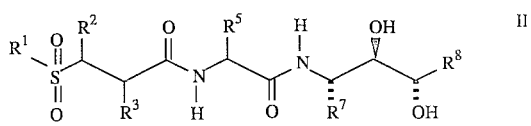

wherein $R^1$ is selected from isopropyl, isobutyl, sec-butyl, tert-butyl, phenyl, fluorophenyl, chlorophenyl, benzyl, fluorobenzyl, chlorobenzyl, naphthyl, fluoronaphthyl, chloronaphthyl, fluoronaphthylmethyl and chloronaphthylmethyl; wherein $R^2$ is selected from hydrido, methyl, ethyl and phenyl; wherein $R^3$ is selected from hydrido, cyclohexylmethyl, benzyl, fluorobenzyl, chlorobenzyl, fluoronaphthylmethyl and chloronaphthylmethyl; wherein each of $R^4$ and $R^6$ is hydrido; wherein each of $R^5$ and $R^8$ is independently selected from $$-(CH_2)_m-C \equiv C-V$$

wherein V is selected from hydrido and methyl; wherein m is one or two; and wherein $R^7$ is cyclohexylmethyl.

The term "hydrido" denotes a single hydrogen atom (H). This hydrido group may be attached, for example, to an oxygen atom to form a hydroxyl group; or, as another example, one hydrido group may be attached to a carbon atom to form a >CH-group; or, as another example, two hydrido groups may be attached to a carbon atom to form a —$CH_2$— group. Where the term "alkyl" is used, either alone or within other terms such as "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The terms "alkoxy" and. "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. Each of the terms "sulfide", "sulfinyl", and "sulfonyl", whether used alone or linked to other terms, denotes, respectively, the divalent radicals

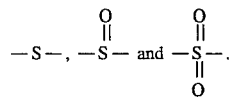

The term "alkenylalkyl" denotes a radical having a double-bond unsaturation site between two carbons, and which radical may consist of only two carbons or may be further substituted with alkyl groups which my optionally contain additional double-bond unsaturation. For any of the foregoing defined radicals, preferred radicals are those containing from one to about fifteen carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups my have one unsaturated bond, such as an allyl group, or may have a plurality of unsaturated bonds, with such plurality of bonds either adjacent, such as allene-type structures, or in conjugation, or separated by several saturated carbons.

Also included in the family of compounds of Formula I are isomeric forms, including diastereoisomers.

Compounds of Formula I would be useful to inhibit enzymatic conversion of angiotensinogen to angiotensin I. When administered orally, a compound of Formula I would be expected to inhibit plasma renin activity and, consequently, lower blood pressure in a mammalian subject (e.g., a human subject). Thus, compounds of Formula I would be therapeutically useful in methods for treating hypertension by administering to a hypertensive subject a therapeutically-effective amount of a compound of Formula I. The phrase "hypertensive subject" means, in this context, a mammalian subject suffering from or afflicted by the effects of hypertension, or susceptible to a hypertensive condition if not treated to prevent or control such hypertension.

Description of the Synthetic Methods for the
Preparation of the Renin Inhibitors of the Invention Synthetic Scheme 1

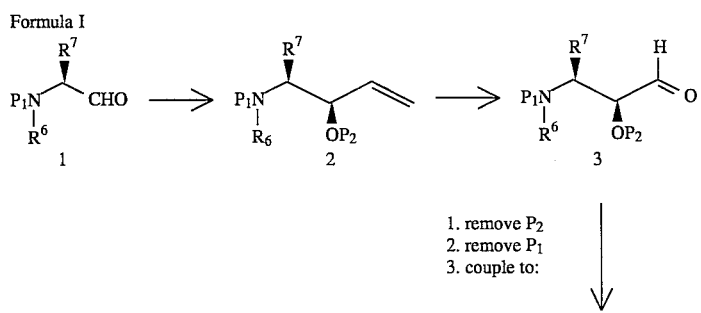

Synthetic Scheme 1

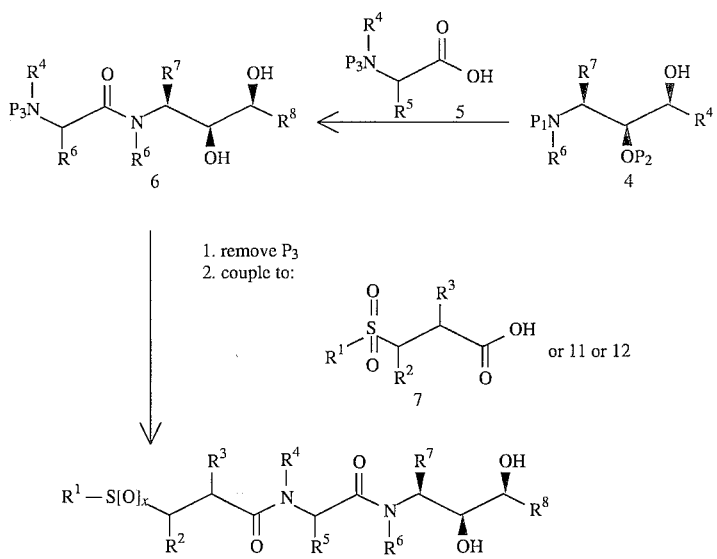

wherein $R^1$ through $R^8$ and x are as defined above.?

A suitably protected amino aldehyde 1 is treated with a Grignard reagent or other organometallic reagent, preferably vinylmagnesium bromide, to obtain the vinyl carbinol 2. This material, suitably protected, is oxidized, preferably with ozone, followed by dimethyl sulfide or zinc treatment, to give intermediate 3. The preceeding process is exemplified in Hanson et al, *J. Org. Chem.*, 50, 5399 (1985). This aldehyde is reacted with an ethynyl-containing organometallic reagent such as propargylmagnesium bromide to give intermediate 4. Compound 4 is deprotected then coupled, using standard amide/peptide coupling methodology to protected triple bond-containing (ethynyl) amino acid derivatives 5 to give compound 6. These standard coupling procedures such as the carbodiimide, active ester (N-hydroxysuccinimide), and mixed carbonic anhydride methods are shown in Benoiton et al, *J. Org. Chem.*, 48, 2939 (1983) and Bodansky et al, "Peptide Synthesis", Wiley (1976). Ethynyl-containing amino-acid derivatives may be prepared by using procedures such as found in Schollkopf, *Tetrahedron Letters*, 39, 2085 (1983). Intermediate 6 is then deprotected, then coupled to intermediate 7, 11 or 12 using the standard amide/peptide coupling methodology, to give compounds of Formula I. Suitable protecting groups may be selected from among those reviewed by R. Geiger in "The Peptides", Academic Press, N.Y. vol. 2 (1979). For example, $P_1$ or $P_3$ may by Boc or Cbz; $P_2$ may be a typical oxygen protective group such as acetyl or t-butyldimethylsilyl.

Synthetic Scheme 2

Preparation of 7:

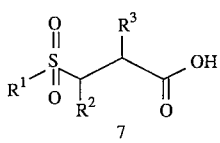

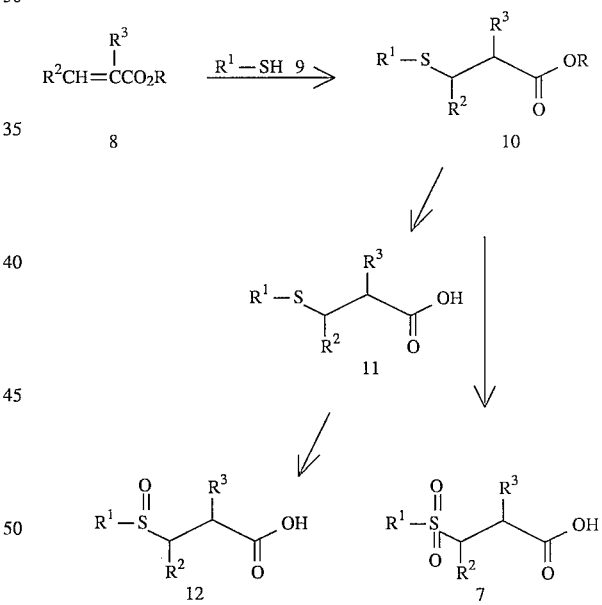

wherein $R^1$, $R^2$ and $R^3$ are as defined above and R is lower alkyl.

Intermediate 7 may be prepared according to Synthetic Scheme 2. Michael addition of a suitable thiol 9 to a suitable acrylic acid 8 in the presence of base catalysts such as sodium hydride, triethyl amine or benzyltrimethylammoniumhydroxide, afforded α,β di-substituted thio-propionic acid alkyl esters 10. In the case of $R^2$= H, a suitable malonic acid dialkyl ester is hydrolyzed to a mono ester, followed by concomitant decarboxylative dehydration to provide α substituted acrylic acid alkyl ester. Compound 10 is converted into its corresponding sulfone acid 7 via base hydrolysis, followed by oxidation with potassium peroxomonosulfate or perbenzoic acid. Compound 10 may also be converted into its corresponding thio-propionic acid 11 via base hydrolysis. Compound 11 then is further converted into its corresponding sulfoxide acid 12 via 3-chloroperbenzoic acid oxidation.

Abbreviations: $P_1$ is an N-protecting group; $P_2$ is H or an oxygen protecting group; $P_3$ is an N-protecting group.

The following Steps 1–13 constitute specific exemplification of methods to prepare starting materials and intermediates embraced by the foregoing generic synthetic schemes. Those skilled in the art will readily understand that known variations of the conditions and processes of the following preparative procedures can be used to prepare the compounds of Steps 1–13. All temperatures expressed are in degrees Centigrade. Compounds of Examples 1–3 may be prepared by using the procedures described in the following Steps 1–13:

Step 1: Preparation of (3S,4S)-N-[(tert-5Butyloxy)-carbonyl]-4-amino-5-phenyl-3-(triisopropylsilyloxy)-pentene A solution of (3S,4S)-N-[(tert.-butyloxy)carbonyl]-4-amino-3-hydroxy-5-phenyl pentene [prepared by the method of Hanson et al, *J. Org, Chem.*, 50, 5399 (1985)] (10.0 g, 64.5 mmol), imidazole (9.14 g, 134 mmol), and chlorotriisopropylsilane (12.44 g, 43.3mmol) in anhydrous DMF (40 mL) was stirred for 5 days at room temperature under an $N_2$ atmosphere. The solution was poured into $H_2O$ (500 mL) and extracted with $Et_2O$ (2×25 mL). The combined organic layers were washed with $H_2O$ (250 mL), a 0.5M citric acid solution (2×120 mL), a 5% $KHCO_3$ solution (2×100 mL), and brine (2×100 mL). After the organic layer was dried over $MgSO_4$, the filtrate was concentrated and purified by medium pressure column chromatography (silica gel, 10% ethyl acetate in hexane, $R_f$ 0.23) to give 12.9 g (82% yield) of the title compound as a clear, colorless oil. $^1H$ and $^{13}C$ NMR spectral data were consistent with the proposed structure.

Step 2: (2R,3S)-N-[(tert-Butyloxy) carbonyl]-3-amino-4-phenyl-2-(triisopropylsilyloxy) butan-1-ol A −78° C. solution of the title compound of Step 1 (12.7 g, 29.3 mmol) in MeOH (81 mL) and $CH_2Cl_2$ (244 mL) was treated with ozone until the solution turned blue. The solution was purged with $O_2$ until the color disappeared and then $NaBH_4$ (3.05 g, 80.5 mmol) was added. After 3 hours at −78° C., the solution was allowed to warmup to room temperature. The reaction solution was poured into $H_2O$ (200 mL) and extracted with ether (3×120 mL). The combined organic layers were washed with brine (2×100 mL) and then dried over $Na_2SO_4$. The filtrate was concentrated to give the title compound as a white solid (13.06 g) . $^1H$ and $^{13}C$ NMR spectral data were consistent with the proposed structure.

Step 3: (2R,3S)-N-[(tert-Butyloxy) carbonyl]-3-amino-4-cyclohexyl-2-(triisopropylsilyloxy) butan-1-ol The alcohol of Step 2 (12.8 g, 29.3 mmol) was dissolved in MeOH (135 mL) and hydrogenated with 5% Rh/C at 60 psi and 60° C. for 30 hours. The filtrate was concentrated and purified by medium pressure column chromatography (silica gel, 15% ethyl acetate in hexane) to give the title compound as a white solid (8.70 g, 67% yield, mp 61°–63° C.). Anal. calcd. for $C_{24}H_{49}NO_4Si$: C, 64.96; H, 11.13; N, 3.16. Found: C, 65.16; H, 11.26; N, 3.12.

Step 4: (2R,3S)-N-[(tert-Butyloxy) carbonyl]-3-amino-4-cyclohexyl-2-(triisopropylsilyloxy) butanal Freshly distilled dimethyl sulfoxide (0.85 g, 10.8 mmol) was added by syringe to a −78° C. solution of oxalyl chloride (0.69 g, 5.41 mmol) in anhydrous THF (22.6 mL). After 10 minutes, the alcohol of Step 3 (2 g, 4.51 mmol) in anhydrous THF (2.3 mL) was added over a period of 1.2 minutes to the −78° C. solution. The solution was stirred for 20 min. and then triethylamine (2.28 g, 22.6 mmol) was added dropwise. The 78° C. bath was removed and the reaction solution was allowed to warm to room temperature. After 1 hour at room temperature, the white, opaque mixture was poured into $H_2O$ (25 mL). The solution was extracted with ether (2×5 mL). The combined organic layers were washed with $^1N$ HCl (25 mL), 5% $NaHCO_3$ (25 mL) and brine (25 mL), and then dried with $MgSO_4$. The filtrate was concentrated at 30° C. in vacuo to give the title compound as a clear, pale yellow liquid (2.08 g, 104% crude yield, TLC, 10% ethyl acetate in hexane, $R_f$ 0.32). $^1H$ and $^{13}C$ NMR spectral data were consistent with the proposed structure.

Step 5: (4S,5R,6S)-N-[(tert-Butyloxy)carbonyl]-6-amino-7-cyclohexyl-4-hydroxy-5-(triisopropylsilyloxy)hept-1-yne To a dry flask under an N2 atmosphere was added Mg (0.40 g, 6.4 mmol), $HgCl_2$ (0.03 g) and anhydrous diethyl ether (4 mL). A solution of 80% propargyl bromide in toluene (1.83 mL, 16.4 mmol) was added to an addition funnel and several drops were added to the reaction mixture. After the reaction was initiated, anhydrous diethyl ether (10 mL) was added to the reaction flask and anhydrous diethyl ether (10 mL) was added to the funnel solution. The funnel solution was added dropwise while the reaction solution was cooled with a 10° C. bath. The white, opaque mixture was stirred at room temperature for 45 minutes and then a solution of aldehyde of Step 4 (2.05 g, 4.64 mmol) in anhydrous diethyl ether (10 mL) was added dropwise. The yellow, opaque mixture was stirred at room temperature for 2 hours. The mixture was cooled to about 0° C. with an ice-water bath and a saturated $NH_4Cl$ solution (25 mL) was added dropwise. The organic layer was collected and the aqueous layer was extracted with diethyl ether (10mL). The combined organic layers were washed with $H_2O$ (10 mL) and brine and then dried over $MgSO_4$. The filtrate was concentrated and purified by medium pressure column chromatography (10% EtOH in hexane, silica gel, $R_f$ 0.20) to give the title compound as a clear, pale yellow liquid (1.49 g, 65% yield). The $^1H$ and $^{13}C$ NMR spectral data were consistent with the proposed structure.

Step 6: (4S,5R,6S)-N-[(tert-Butyloxy) carbonyl]-6-amino-7-cyclohexyl-4,5-dihydroxyhept-1-yne A solution of the silane of Step 5 in 1.0 M tetrabutylammonium fluoride in tetrahydrofuran (21.5 mL, 21.5 mmol) was stirred at room temperature for 60 minutes. The reaction solution was concentrated in vacuo. The concentrate was dissolved in ethyl acetate (160 mL) and was washed with $H_2O$ (3×60 mL) and brine (1×100 mL). After the organic layer was dried with $MgSO_4$, the filtrate was concentrated and purified by medium pressure column chromatography (silica gel, 30% EtOAc in hexane) to give the title compound as a clear, colorless oil (0.93 g, 53%, $R_f$ 0.16) along with 0.35 g of the epimer (20% yield; $R_f$ 0.04). $^1H$ and $^{13}C$ NMR

Step 7: (4S, 5R, 6S) -6-amino-7-cyclohexyl-4,5-dihydroxyhept-1-yne

A solution of compound of Step 6 (0,926 g, 2.85 mmol) and trifluoroacetic acid (5.49mL, 71.3mmol) in $CH_2Cl_2$ (5.49 mL) was stirred at room temperature for 30 minutes and then concentrated in vacuo. The residue was dissolved in 1.0 N KOH (7 mL) and extracted with ethyl acetate (4×10 mL). The combined organic layers were dried over $MgSO_4$ and then concentrated to give the title amine as an off-white solid (0.67 g, 100% yield). $^1H$ and $^{13}C$ NMR spectral data were consistent with the proposed structure.

Step 8: Preparation of L-Boc-C-propargylglycine

L-C-propargylglycine (10 g) [prepared by the method of Schwyzer et al, *Helvetia Chimica Acta.*, 59, 2181 (1976)] was suspended in tetrahydrofuran (30 mL). Water (30 mL), potassium carbonate (36.7 g), and di-tert-butyl-dicarbonate (21.9 g) were added. Additional water was added to produce a solution which was stirred for 12 hours at room temperature. The organic solvent was then evaporated and the aqueous solution was washed with ether, then acidified to pH 3 with 1N aqueous citric acid. The solution was extracted with methylene chloride and the solvent evaporated to give the title compound (18.9 g, 97% yield), which was used without further purification.

Step 9: Preparation of L-Boc-C-propargylglycine amide of (4S,5R,6S)-6-amino-7-cyclohexyl-4,5-dihydroxyhept-1-yne L-Boc-C-propargylglycine (1.2 g) was dissolved in methylene chloride (5 mL) and N-methyl piperidine (0.57 g) was added. The mixture was cooled to zero degrees centigrade and isobutyl chloroformate (0.78 g) was added. The mixture was stirred for 10 minutes whereupon the title compound of Step 7 (1.4 g) in methylene chloride (5 mL) and tert-butyl alcohol (5 mL) was added and this mixture stirred for 15 minutes at 0° C. and 4° C. for 12 hours. The reaction mixture was washed successively with 1N citric acid, saturated sodium hydrogen carbonate, water and brine. The organic layer was dried over magnesium sulfate and evaporated to dryness. The residue was chromatographed on silica gel to give the title compound as a colorless oil. $^1H$ NMR: 300 MHz spectrum consistent with proposed structure.

Step 10: Preparation of L-C-propargylglycine amide of (4S,5R,6S)-6-amino-7-cyclohexyl-4,5-dihydroxyhept-1-yne The title compound of Step 9 (0.76 g) was dissolved in a mixture of trifluoroacetic acid (4.9 mL) and methylene chloride (4.9 mL), and stirred for 30 minutes at room temperature. The solvent was then evaporated and the residue taken up in ethyl acetate. The organic layer was washed with saturated sodium hydrogen carbonate, water and brine, then dried over magnesium sulfate and evaporated to give the title amine. $^1HNMR$: 300 MHz spectrum consistent with proposed structure.

Step 11: Preparation of R,S-2-Benzyl-3-tert-butylsulphonyl-proionic acid

The title compound of Step 11 was prepared by procedures described in Step 11 (a) to (d), below:

Step 11(a): Preparation of α-benzylacrylic acid ethyl ester

A mixture of 4.0 g of KOH in 50 ml of ethanol was added at room temperature to 20 g of benzylmalonic acid diethyl ester in 40 ml of ethanol. The mixture was stirred overnight at room temperature, then concentrated by evaporation, thereafter 7.1 ml of water was added and then the mixture was acidified in an ice bath with 6.3 ml of concentrated hydrochloric acid. Partitioning between water and ether was carried out, the organic phase was dried and the ether was distilled off. Then, 12.9 ml of pyridine, 0.61 g of piperidine and 1.78 g of paraformaldehyde were added to the residue. The mixture was heated in an oil bath (130°) for 90 minutes, cooled, 220 ml of water was added and extraction was carried out 3 times with 75 ml of n-hexane. The combined organic phases were washed alternatively with water, $^1N$ HCl, water, saturated $NaHCO_3$ solution and brine. The solution was dried ($MgSO_4$) and evaporated to give the title compound as colorless oil (26 g, 85% yield) $^1HNMR$: 300MHz; spectrum consistent with proposed structure.

Step 11(b): Preparation of 2-benzyl-3-tert.-butylthio-propionic acid ethyl ester 4.0 g of α-benzylacrylic acid ethyl ester was dissolved in 40 ml of THF and reacted at room temperature with a mixture of 2.39 ml of tert.-butylmercaptan and 459 mg of sodium hydride dispersion (60% in oil). The mixture was stirred at room temperature for 5 hours, poured into 1N hydrochloric acid and extracted with ethyl acetate. The extracts were dried and concentrated by evaporation. The residue was purified by flash chromatography on silica gel, eluting with hexane-ethyl acetate (8:1). Colorless oil (4 g, 68% yield). $^1H$ NMR: 300MHz spectrum consistent with proposed structure. Anal. calcd. for $C_{16}H_{24}O_2S$: C, 68.53; H, 8.63. Found, C, 68.10; H, 8.47.

Step 11(c): Preparation of 2-benzyl-3-tert.-butylthio-propionic acid 400 mg of 2-benzyl-3-tert.-butylthio-propionic acid ethyl ester was dissolved in 1.5 ml of methanol and then reacted with 5 ml of 2N potassium hydroxide solution. The mixture was stirred overnight at room temperature and concentrated by evaporation. The residue was diluted with water and washed with ether. The aqueous layer was acidified to pH 3 with 2N HCl, and then evaporated to give the title compound (280mg, 78% yield). $^1H$ NMR: 300MHz spectrum consistent with proposed structure.

Step 11(d): Preparation of 2-benzyl-3-tert.-butylsulfonyl-propionic acid 280 mg of 2-benzyl-3-tert.-butylthio-propionic acid was dissolved in 5 ml of methanol and, while cooling with ice, 1 g of potassium peroxomonosulfate in 4 ml of water was added and the whole was stirred overnight at room temperature. The solution was diluted with water and extracted with methylene chloride, and the extracts were dried and concentrated by evaporation (260 mg, 82% yield). $^1H$ NMR: 300MHz spectrum consistent with proposed structure. Anal. calcd. for $C_{14}H_{20}O_4S$: C, 59.13; H, 7.09. Found: C, 59.39;

spectral data for the title compound ($R_f$ 0.16) was consistent with the proposed structure. Anal. calcd. for $C_{18}H_{31}NO_4$: C, 66.43; H, 9.60; N, 4.30: Found: C, 66.00; H, 9.70; N, 4.20.

H, 7.08.

Step 12: Preparation of
R,S-2-Benzyl-3-isobutylsulfonyl-propionic acid

The same procedures for the preparation of the title compound of Step 11 may be applied to the preparation of the title compound of Step 12 by substituting isobutyl mercaptan for t-butyl mercaptan in Step 11b.

Step 13: Preparation of
R,S-2-Benzyl-3-phenylsulfonyl-propionic acid

The same procedures for the preparation of the title compound of Step 11 may be applied to the preparation of the title compound of Step 13 by substituting thiophenol for t-butyl mercaptan in Step 11b.

The following working Examples are provided to illustrate synthesis of Compounds 1–36 of the present invention and are not intended to limit the scope thereof. Those skilled in the art will readily understand that known variations of the conditions and processes of the following preparative procedures can be used to prepare the compounds of the Examples. All temperatures expressed are in degrees Centigrade.

EXAMPLE 1

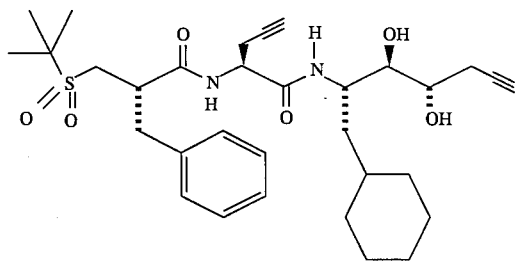

N-[[1R*-[[1S,1R*-(cyclohexylmethyl)-2S*,3R*-dihydroxy-5-hexynyl]amino]carbonyl]-3butynyl]-α
R*-[[(1,1-dimethylethyl)sulfonyl]methyl]
benzenepropanamide The title compound of Step 11 (2.67 mmol) is dissolved at room temperature in a mixture of dimethylfonnamide (11 mL) and pyridine (2 mL) and to this solution is added N,N'-disuccinimidyl carbonate (2.43 mmol) and 4-dimethylaminopyridine (30 mg). The mixture is stirred for 3 hours, and then the title amine of Step 10 (2.43 mmol) is added. This mixture is allowed to stir for 12 hours. The solvent is then evaporated and the residue dissolved in ethyl acetate (60 mL). The mixture is washed successively with water, 0.5M citric acid saturated sodium bicarbonate and brine, then dried over sodium sulfate and the solvent evaporated. The residue is purified by flash chromatography on silica gel remove the undesired diastereomer to give the title compound as a white or off-white powder.

EXAMPLE 2

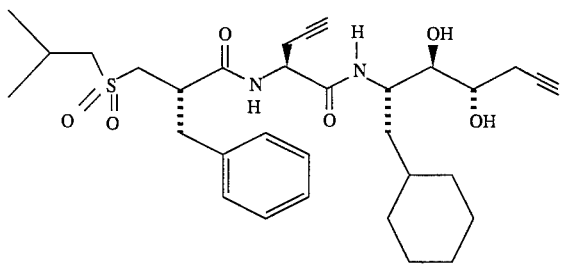

N-[[1R*-[[1S,1R*-(cyclohexylmethyl)-2S*,3R*-dihydroxy-5-hexynyl]amino]carbonyl]-3butynyl]-α
R*-[[(2-methylpropyl)sulfonyl]methyl]
benzenepropanamide The title compound of Step 12 (2.67 mmol) is dissolved at room temperature in a mixture of dimethylformamide (11 mL) and pyridine (2 mL) and to this solution is added N,N'-disuccinimidyl carbonate (2.43 mmol) and 4-dimethylaminopyridine (30 mg). The mixture is stirred for 3 hours, and then the title amine of Step 10 (2.43 mmol) is added. This mixture is allowed to stir for 12 hours. The solvent is then evaporated and the residue dissolved in ethyl acetate (60 mL). The mixture is washed successively with water, 0.5M citric acid saturated sodium bicarbonate and brine, then dried over sodium sulfate and the solvent evaporated. The residue is purified by flash chromatography on silica gel remove the undesired diastereomer to give the title compound as a white or off-white powder.

EXAMPLE 3

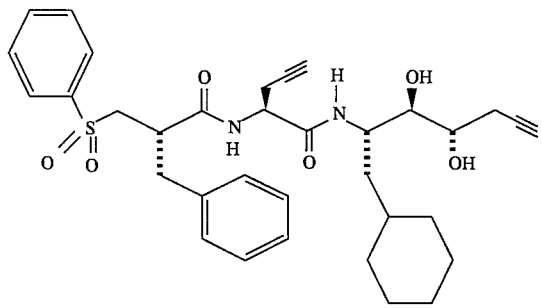

N-[[1R*-[[1S,1R*-(cyclohexylmethyl)-2S*,3R*-dihydroxy-
5-hexynyl]amino]carbonyl]-3butynyl]-αR*-[
(phenylsulfonyl)methyl]benzenepropanamide The title compound of Step 13 (2.67 mmol) is dissolved at room temperature in a mixture of dimethylformamide (11 mL) and pyridine (2 mL) and to this solution is added N,N'-disuccinimidyl carbonate (2.43 mol) and dimethylaminopyridine (30 mg). The mixture is stirred for 3 hours, and then the title amine of Step 10 (2.43 mmol) is added. This mixture is allowed to stir for 12 hours. The solvent is then evaporated and the residue dissolved in ethyl acetate (60 mL). The mixture is washed successively with water, 0.5M citric acid saturated sodium bicarbonate and brine, then dried over sodium sulfate and the solvent evaporated. The residue is purified by flash chromatography on silica gel remove the undesired diastereomer to give the title compound as a white or off-white powder.

Compounds #4–36, as shown in Table I below, may be synthesized by reference to the foregoing specific and general procedures for preparing compounds of Formula I.

TABLE I

| Example Compound No. | Structure |
|---|---|
| 4 | 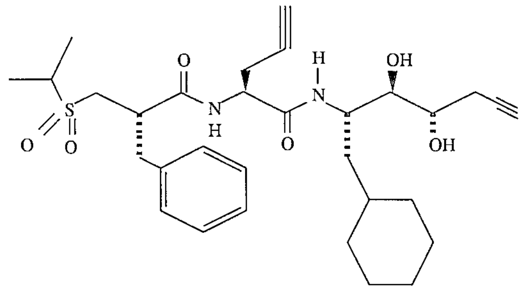 |
| 5 | 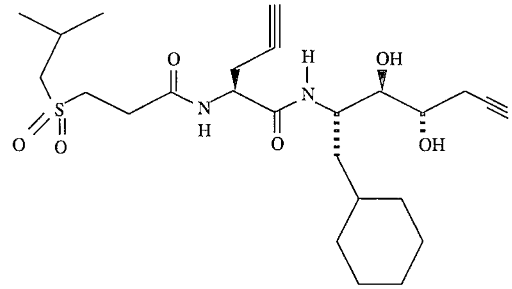 |
| 6 | 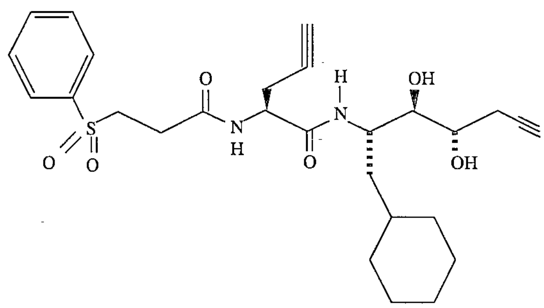 |
| 7 | 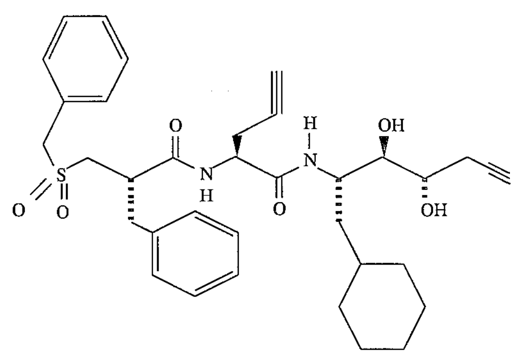 |

TABLE I-continued
| Example Compound No. | Structure |
|---|---|
| 8 | 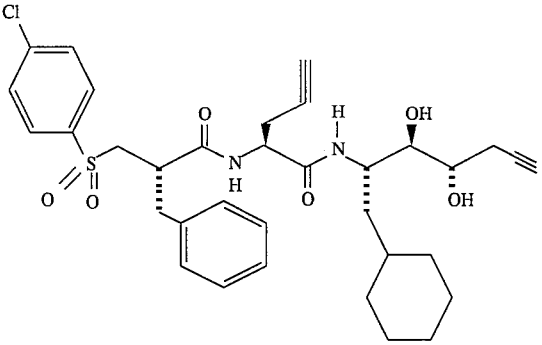 |
| 9 | 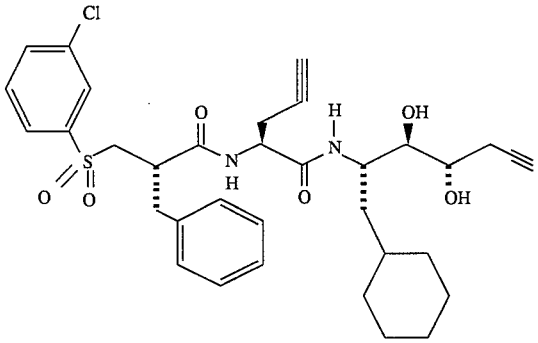 |
| 10 | 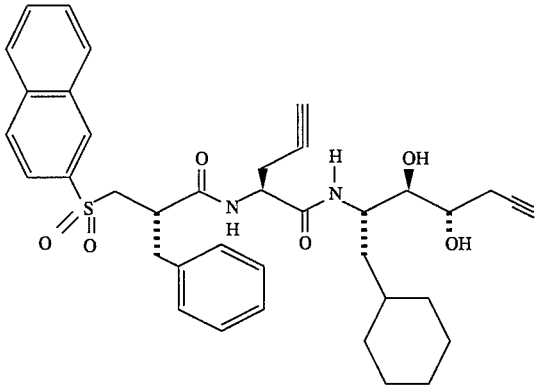 |
| 11 | 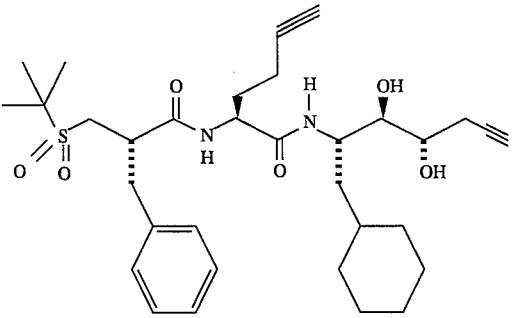 |

TABLE I-continued

| Example Compound No. | Structure |
| --- | --- |
| 12 | 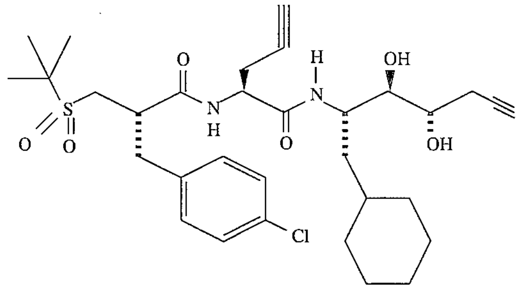 |
| 13 | 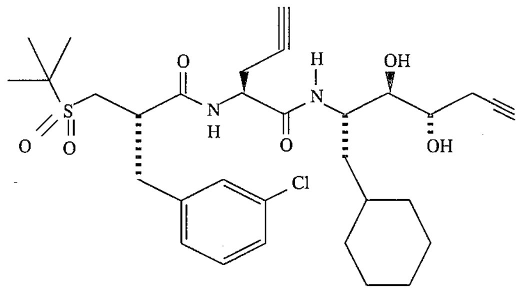 |
| 14 | 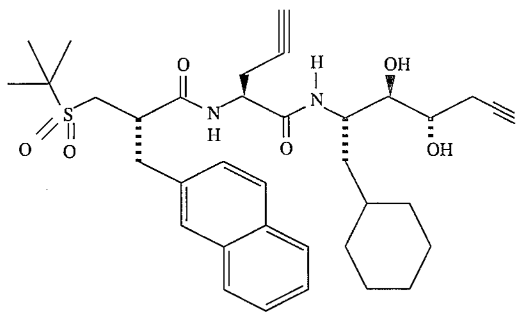 |
| 15 | 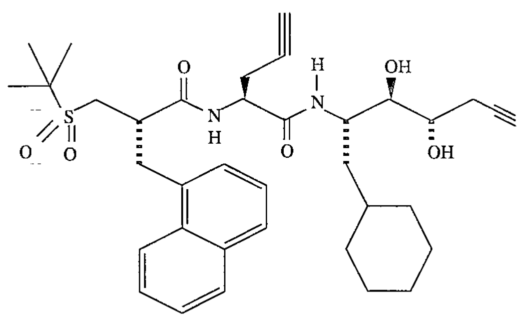 |
| 16 | 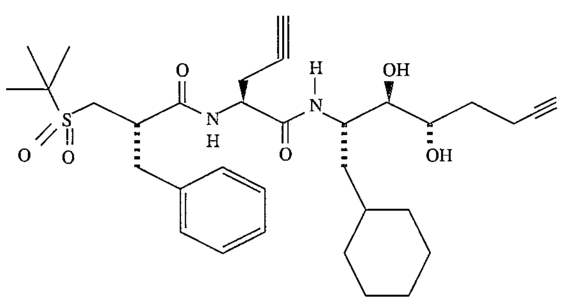 |

TABLE I-continued

| Example Compound No. | Structure |
| --- | --- |
| 17 | 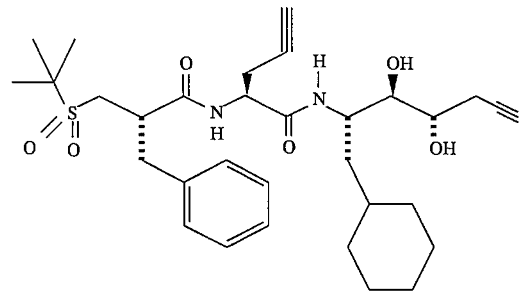 |
| 18 | 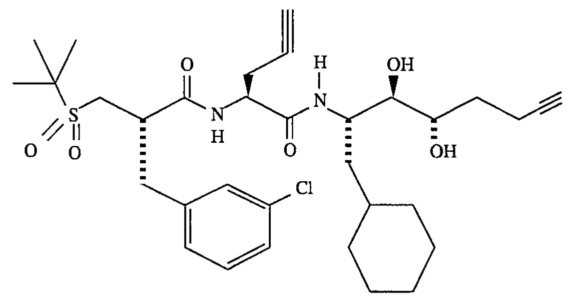 |
| 19 | 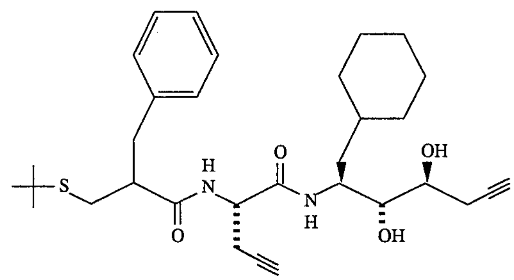 |
| 20 | 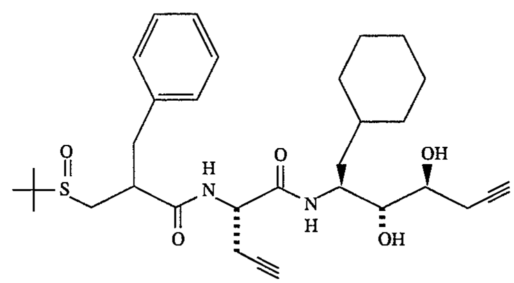 |
| 21 | 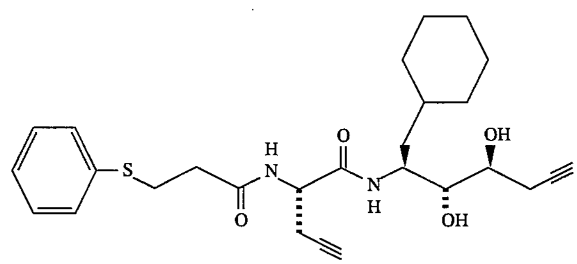 |

TABLE I-continued

| Example Compound No. | Structure |
|---|---|
| 22 | 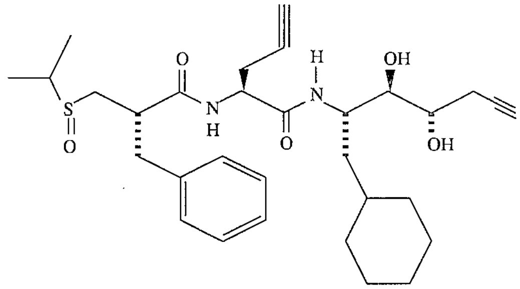 |
| 23 | 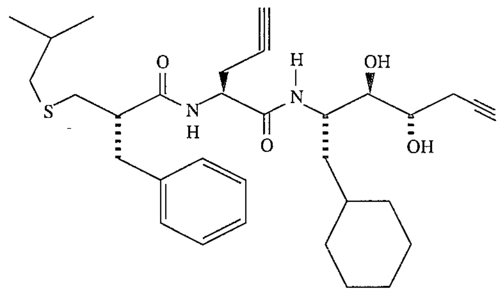 |
| 24 | 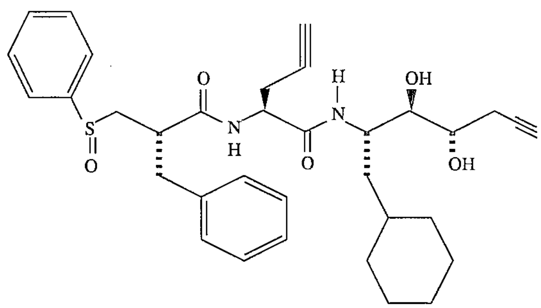 |
| 25 | 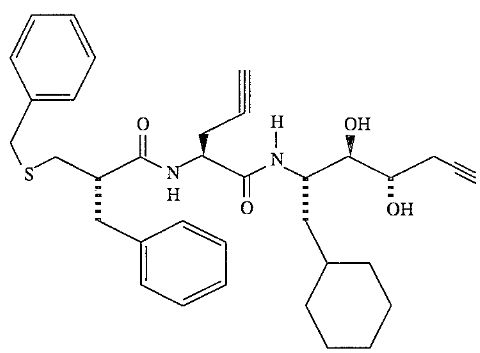 |
| 26 | 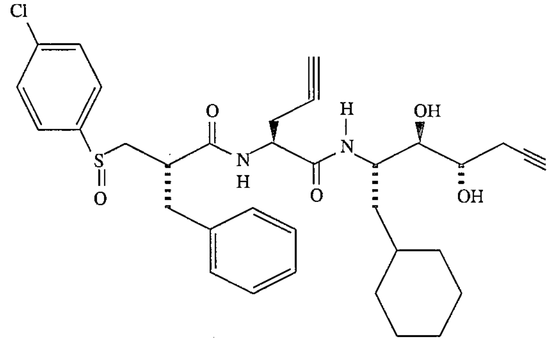 |

TABLE I-continued
| Example Compound No. | Structure |
|---|---|
| 27 | 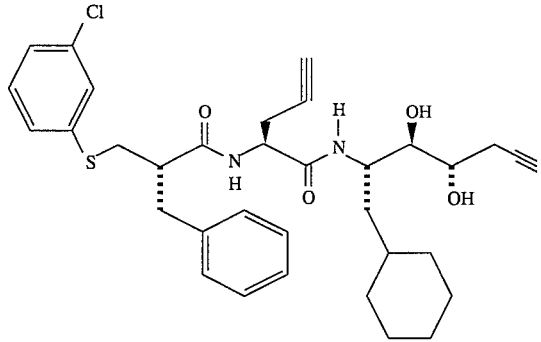 |
| 28 | 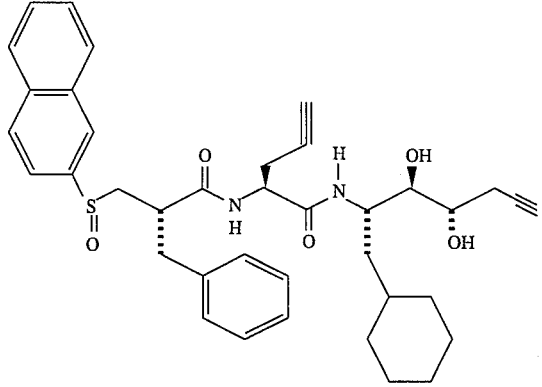 |
| 29 | 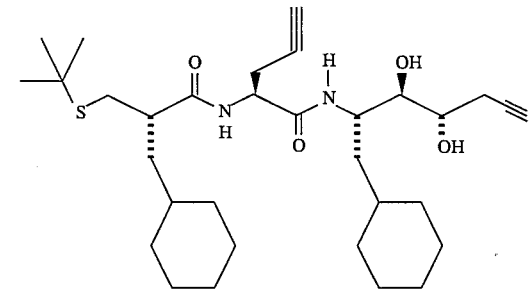 |
| 30 | 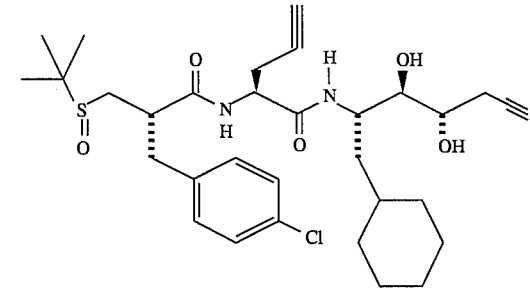 |

TABLE I-continued

| Example Compound No. | Structure |
| --- | --- |
| 31 | 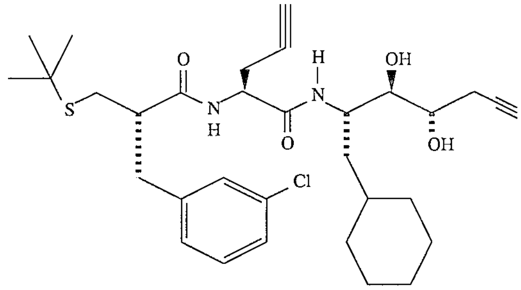 |
| 32 | 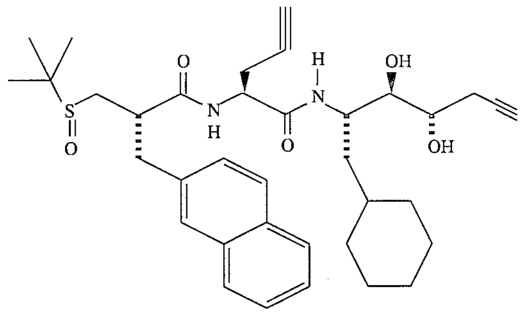 |
| 33 | 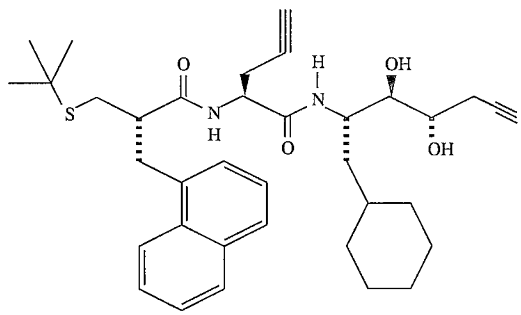 |
| 34 | 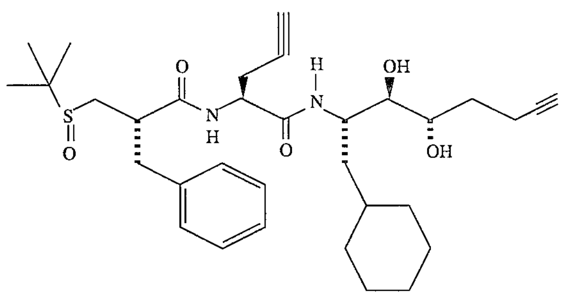 |
| 35 | 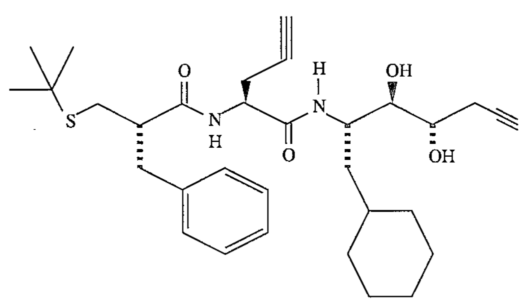 |

TABLE I-continued

| Example Compound No. | Structure |
|---|---|
| 36 | (structure image) |

BIOLOGICAL EVALUATION

Human Renin Inhibition in vitro

Compounds of Formula I may be evaluated as inhibitors of human renin in an in vitro assay, as follows: This human renin inhibition test has been previously described in detail [Papaioannou et al., *Clinical and Experimental Hyperpension*, A7(9), 1243–1257 (1985)]. Human renin was obtained from the National Institute for Biological Standards, London. An incubation mixture was prepared containing the following components: in a total volume of 0.25 mL: 100 mM Tris-acetate buffer at pH 7.4, $25 \times 10^{-6}$ Goldblatt units of renin, 0.05 mL of plasma from human volunteers taking oral contraceptives, 6.0 mMNa-EDTA, 2.4 mM phenylmethyl sulfonyl fluoride, 1.5 mM 8-hydroxyquinoline, 0.4 mg/mL bovine serum albumin (BSA), and 0.024 mg/mL neomycin sulfate. This mixture was incubated for two hours at 37° C. in the presence or absence of renin inhibitors. The produced angiotensin I was determined by radioimmunoassay (New England Nuclear kit). Test compounds to be assayed were dissolved in DMSO and diluted with 100 mM Tris-acetate buffer at pH 7.4 containing 0.5% BSA to the appropriate concentration. The final concentration of organic solvent in the reaction mixture was less than 1%. Control incubations at 37° C. were used to correct for effects of organic solvent on renin activity. The in vitro enzymatic conversion of angiotensinogen to angiotensin I would be expected to be inhibited by test compounds of the invention.

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 400 mg of active compound per unit dosage form. A more preferred dosage will contain from about 2 mg to about 200 mg of active compound per unit dosage form. Most preferred is a dosage form containing from about 3 mg to about 100 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A therapeutic method for treating a disease, other than hypertension, mediated by plasma renin activity in a subject in need thereof, said method comprising administering to said subject a therapeutically-effective amount of a renin-inhibiting compound of Formula I:

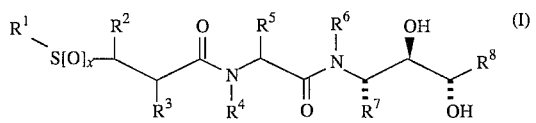

wherein $R^1$ is a group selected from alkyl, trifluoromethyl, cycloalkyl, cycloalkylalkyl, aryl, haloaryl, aralkyl and haloaralkyl; wherein x is a number selected from zero, one and two; wherein $R^2$ is selected from hydrido and alkyl; wherein $R^3$ is a group selected from hydrido, cycloalkylalkyl, aralkyl and haloaralkyl; wherein each of $R^4$ and $R^6$ is a group independently selected from hydrido and methyl; wherein each of $R^5$ and $R^8$ is independently selected from

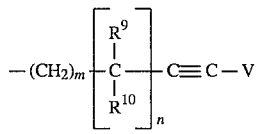

wherein V is selected from hydrido, alkyl, cycloalkyl, aryl and aralkyl; wherein each of $R^9$ and $R^{10}$ is a group independently selected from hydrido, alkyl, alkenyl, alkynyl, cycloalkyl and aryl; wherein m is a number selected from zero through three; wherein n is a number selected from zero through three; wherein $R^7$ is a group selected from alkyl, cycloalkylalkyl and aralkyl; and wherein any one of said $R^1$ through $R^{10}$ groups having a substitutable position may be substituted with one or more groups selected from alkyl, hydroxy, alkoxy and alkenyl.

2. The method of claim 1 wherein $R^1$ is selected from alkyl, trifluoromethyl, cycloalkyl, cycloalkylalkyl, phenyl, halophenyl, phenylalkyl, halophenylalkyl, naphthyl, halonaphthyl, naphthylaklyl and halonaphthylalkyl; wherein x is a number selected from zero, one and two; wherein $R^2$ is selected from hydrido and alkyl; wherein $R^3$ is selected from hydrido, cycloalkylalkyl, phenylalkyl, halophenylalkyl, naphthylalkyl and halonaphthylalkyl; wherein each of $R^4$ and $R^6$ is independently selected from hydrido and methyl; wherein each of $R^5$ and $R^8$ is independently selected from

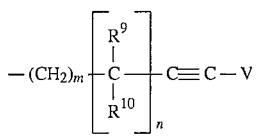

wherein V is selected from hydrido, alkyl, phenyl and benzyl; wherein each of $R^9$ and $R^{10}$ is independently selected from hydrido, alkyl, alkenyl, alkynyl, cycloalkyl and aryl; wherein m is a number selected from zero through three; wherein n is a number selected from zero through three; and wherein $R^7$ is selected from cyclohexylmethyl and benzyl, either one of which may be substituted with one or more groups selected from alkyl, hydroxy and alkoxy.

3. The method of claim 2 wherein $R^1$ is selected from methyl, ethyl, n-propyl, isopropyl, n-butyl, isobutyl, sec-butyl, tert-butyl, trifluoromethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is a number selected from zero, one and two; wherein $R^2$ is selected from hydrido, methyl, ethyl and n-propyl; wherein $R^3$ is selected from hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is independently selected from hydrido and methyl; wherein each of $R^5$ and $R^8$ is independently selected from

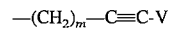

wherein V is selected from hydrido and alkyl; wherein m is a number selected from one through three; and wherein $R^7$ is cyclohexylmethyl.

4. The method of claim 3 wherein $R^1$ is selected from methyl, ethyl, n-propyl, isopropyl, benzyl, phenethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is zero or two; wherein $R^2$ is selected from hydrido, methyl, ethyl and n-propyl; wherein $R^3$ is selected from hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is hydrido; wherein each of $R^5$ and $R^8$ is independently selected from

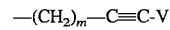

wherein V is selected from hydrido and methyl; wherein m is one or two; and wherein $R^7$ is cyclohexylmethyl.

5. The method of claim 4 wherein said compound is selected from compounds of Formula II

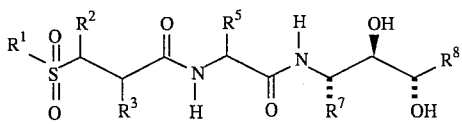

II wherein $R^1$ is selected from isopropyl, isobutyl, sec-butyl, tert-butyl, phenyl, fluorophenyl, chlorophenyl, benzyl, fluorobenzyl, chlorobenzyl, naphthyl, fluoronaphthyl, chloronaphthyl, fluoronaphthylmethyl and chloronaphthylmethyl; wherein $R^2$ is selected from hydrido, methyl, ethyl and phenyl; wherein $R^3$ is selected from hydrido, cyclohexylmethyl, benzyl, fluorobenzyl, chlorobenzyl, fluoronaphthylmethyl and chloronaphthylmethyl; wherein each of $R^4$ and $R^6$ is hydrido; wherein each of $R^5$ and $R^8$ is independently selected from

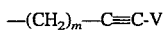

wherein V is selected from hydrido and methyl; wherein m is one or two; and wherein $R^7$ is cyclohexylmethyl.

6. The method of claim 5 wherein said compound is N-[[1R*-[[1S, 1R*-(cyclohexylmethyl) -2S*, 3R*-dihydroxy-5-hexynyl] amino]carbonyl]-3-butynyl]-αR*-[[(1,1-dimethylethyl)sulfonyl]-methyl] benzenepropanamide.

7. The method of claim 5 wherein said compound is N-[[1R*-[[1S,1R*-(cyclohexylmethyl)-2S*,3R*-dihydroxy-5-hexynyl] amino]carbonyl]-3-butynyl]-αR*-[[(2-methylpropyl)sulfonyl] methyl]benzenepropanamide.

8. The method of claim 5 wherein said compound is N-[[1R*-[[1S, 1R*-(cyclohexylmethyl)-2S*,3R*-dihydroxy-5-hexynyl] amino]carbonyl]-3-butynyl]-αR*-[(phenylsulfonyl)methyl] benzenepropanamide.

9. The method of claim 1 comprising administering said renin-inhibiting compound intramuscularly to a subject.

10. The method of claim 1 comprising administering said renin-inhibiting compound topically to a subject.

* * * * *